(12) United States Patent
Eszter et al.

(10) Patent No.: US 8,501,422 B2
(45) Date of Patent: Aug. 6, 2013

(54) METHODS OF DETECTING AND TREATING PULMONARY DISEASE AND MARKERS THEREOF

(75) Inventors: Csanky Eszter, Debrecen (HU); Ralph Ruhl, Debrecen (HU); Laszlo Takacs, Newburry Park, CA (US); William Hempel, Antony (FR)

(73) Assignee: F. Hoffman-La Roche SA, Basel (CH)

( * ) Notice: Subject to any disclaimer, the term of this patent is extended or adjusted under 35 U.S.C. 154(b) by 187 days.

(21) Appl. No.: 13/120,189

(22) PCT Filed: Sep. 23, 2009

(86) PCT No.: PCT/EP2009/062324
§ 371 (c)(1),
(2), (4) Date: Jul. 28, 2011

(87) PCT Pub. No.: WO2010/034742
PCT Pub. Date: Apr. 1, 2010

(65) Prior Publication Data
US 2012/0021532 A1    Jan. 26, 2012

Related U.S. Application Data

(60) Provisional application No. 61/099,963, filed on Sep. 25, 2008.

(51) Int. Cl.
*G01N 31/00*    (2006.01)
*G01N 33/53*    (2006.01)

(52) U.S. Cl.
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

FOREIGN PATENT DOCUMENTS
WO    WO 02/092073    11/2002
WO    WO 2005/115374    12/2005

OTHER PUBLICATIONS

Babcock, T. et al. "Eicosapentanoic Acid (EPA): An Antiinflammatory ω-3 Fat With Potential Clinical Applications" *Nutrition*, Jan. 1, 2000, pp. 1116-1118, vol. 16, No. 11/12.

Shahar, E. et al. "Docosahexaenoic Acid and Smoking-Related Chronic Obstructive Pulmonary Disease" *American Journal of Respiratory and Critical Care Medicine*, Jun. 1999, pp. 1780-1785, vol. 159, No. 6.

*Primary Examiner* — Lisa Cook
(74) *Attorney, Agent, or Firm* — Saliwanchik, Lloyd & Eisenschenk

(57) ABSTRACT

The present invention relates to the treatment of pulmonary diseases. More specifically, the invention relates to new methods of detecting and treating chronic obstructive pulmonary disease (COPD). In particular, the invention relates to a method of measuring one or more lipid metabolites in human body fluids as an indicator/biomarker of the progress of chronic obstructive pulmonary disease. The present invention also relates to a method of detecting and/or monitoring chronic obstructive pulmonary disease in a subject, the method comprising measuring the level of at least one lipid metabolite in a sample from the subject, wherein said level is indicative of COPD. The present invention also relates to a method of assessing the efficacy of a COPD treatment in a subject, the method comprising a step of measuring the level of at least one lipid metabolite in a sample from the subject, wherein said level is indicative of COPD severity or status.

19 Claims, 3 Drawing Sheets

METHODS OF DETECTING AND TREATING PULMONARY DISEASE AND MARKERS THEREOF

CROSS-REFERENCE TO RELATED APPLICATIONS

Figure 1:
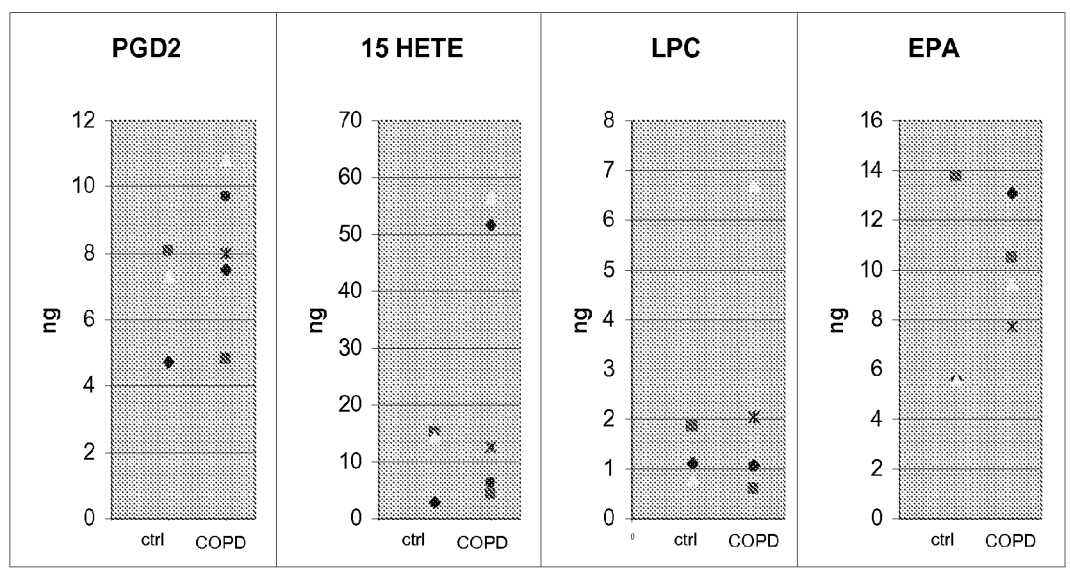

This application is the U.S. national stage application of International Patent Application No. PCT/EP2009/062324, filed Sep. 23, 2009, which claims the benefit of U.S. Provisional Patent Application No. 61/099,963, filed Sep. 25, 2008, the disclosures of which are hereby incorporated by reference in their entireties, including all figures, tables and amino acid or nucleic acid sequences.

FIELD OF THE INVENTION

The present invention relates to the treatment of pulmonary diseases. More specifically, the invention relates to new methods of detecting and treating chronic obstructive pulmonary disease (COPD). In particular, the invention relates to a method of measuring one or more lipid metabolites in human body fluids as an indicator/biomarker of the progress of chronic obstructive pulmonary disease.

BACKGROUND OF THE INVENTION

Chronic obstructive pulmonary disease (COPD) commonly caused by smoking is a leading cause of morbidity and mortality worldwide and is currently the 5th leading cause of death in the westernized world [Rabe et al., 2007]. The World Health Organization (WHO) predicts that by 2020 COPD will rise from being the twelfth to the $5^{th}$ most prevalent disease worldwide, and to the $3^{rd}$ most common cause of death [Rabe et al., 2007]. Unlike asthma, where the relative understanding of the underlying pathophysiological mechanisms and clinical management of the disease are quite advanced, the same cannot be said for COPD, due to the complexity of the disease and the fact that it has only recently become the focus of clinical and basic research.

COPD is characterized by the slowly progressive development of poorly reversible airflow limitation. The disease includes chronic bronchitis with fibrosis and obstruction of small airways, emphysema leading to the enlargement of airspaces and destruction of lung parenchyma, and loss of lung elasticity [Rennard et al., 2002].

Disease pathology is reflected by chronic inflammatory processes as the obstruction of airways due to inflammatory cell infiltration and fibrosis along with inflammatory exudates in the lumen correlate with the severity of airflow obstruction [Hogg et al., 2004]. Hence, a large amount of research effort has focused on mediators of inflammation, the cells which secrete them, and their targets in the airways [Barnes et al., 2004].

The diagnosis of COPD is built upon the symptoms of cough and sputum production and/or exercise induced dyspnea along with a decreasing level of lung function as tested by spirometry (Global Initiative for Chronic Obstructive Lung Disease, Global strategy for the diagnosis, management and prevention of Chronic Obstructive Lung Disease. www.gold-copd.com).

Because most patients first seek treatment when lung damage is already extensive (stage II COPD), there is a need for earlier disease detection and for a disease management tool [Csanky et al., 2007]. Economic and practical arguments justify the search for simple diagnostic tests, applicable in bedside or outpatient center settings, to replace the costly imaging technology and impractical spirometric tests used in hospitals and larger clinical centers.

One step global profiling of analyte (mRNA, protein, metabolite) biomarkers may soon replace conventional blood and histological/biopsy diagnostics technologies. It is important to establish whether the numerous blood and other body fluid derived potential novel diagnostics will be sufficiently efficacious and precise to replace, for example, imaging and functional diagnostic tests.

Currently, imaging technologies and spirometry are indispensable for the diagnosis and management of COPD. Both the diagnosis and management of COPD rely on costly and labor intensive lung function tests. Thus, there is an imminent need to replace the current diagnostic approaches with simpler clinical assays.

Amongst the many different classes of inflammatory mediators which have been suggested to play a role in COPD, lipid mediators derived from phospholipase metabolites appear to play an important role. We chose a set of precursor and end-stage, biologically active lipid metabolites and tested these in the BAL fluid of COPD patients and controls by mass spectrometry based quantitative methods.

As a first approach we focused on the BAL fluid which we obtained via a relatively invasive (bronchoscopy) albeit frequently used in diagnostic procedure. Bronchoaveolar lavage allows examination of the disease process "in-situ" by allowing the sampling of metabolites deep in the tissue at the level of bronchioles and alveolar ducts. We demonstrate the presence of a set of lipid metabolites that were measurable in the BAL fluid and support our goals to establish a correlation between lung function test results and lipid biomarker levels.

SUMMARY OF THE INVENTION

The present invention relates to a method of measuring one or more lipid metabolites in human body fluids as an indicator/biomarker of the progress of chronic obstructive pulmonary disease (COPD).

The present invention also relates to a method of detecting and/or monitoring chronic obstructive pulmonary disease (COPD) in a subject, the method comprising measuring the level of at least one lipid metabolite in a sample from the subject, wherein said level is indicative of COPD.

Another aspect of the present invention relates to a method of assessing the efficacy of a COPD treatment in a subject, the method comprising a step of measuring the level of at least one lipid metabolite in a sample from the subject, wherein said level is indicative of COPD severity or status.

LEGEND OF THE FIGURES

FIG. 1: Level of lipids measured in BAL fluid of control and COPD patients.

Figure 2:
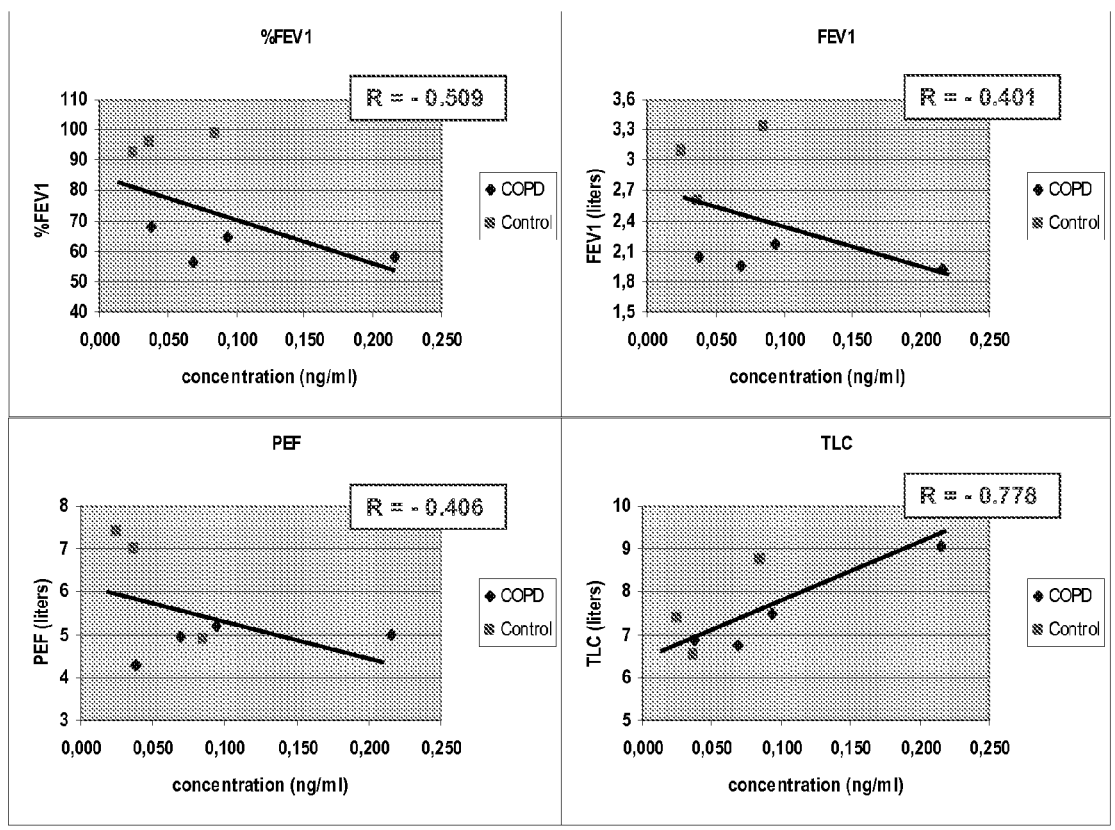

FIG. 2: Concentration of PgD2 measured in BAL fluid plotted against lung function values.

Figure 3:
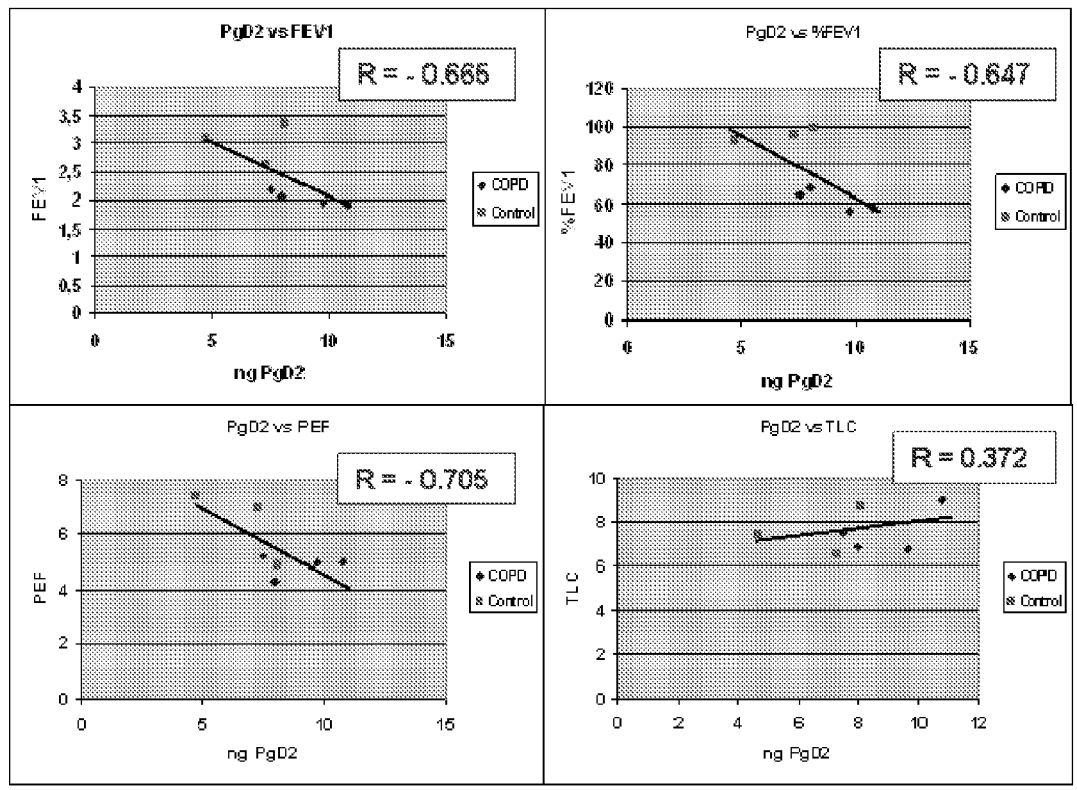

FIG. 3: Plots of $PgD_2$ levels in BAL fluid versus lung function parameter values.

Figure 4:
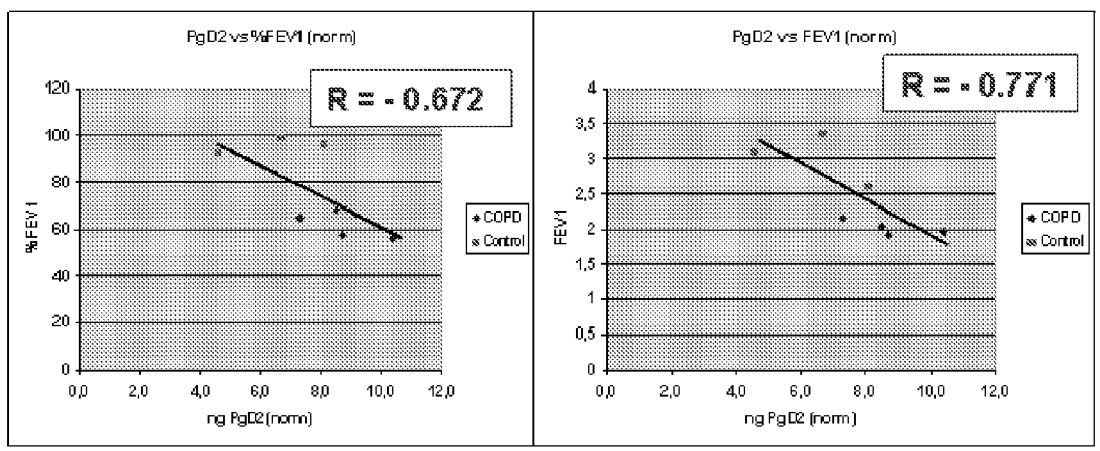

FIG. 4: Plots of $PgD_2$ levels in BAL fluid versus lung function parameter values after normalization for total lung capacity.

DETAILED DESCRIPTION OF THE INVENTION

The present invention proposes for the first time using body fluid biomarkers for detecting COPD. In particular, following the measure of the level of a number of biologically relevant lipids and metabolites in the bronchoalveolar lavage (BAL)

fluid of COPD and control subjects, the inventors have shown that lipid biomarker levels correlate with lung function.

In the apparently BAL accessible fluid compartment, the total recovered lipid metabolite amount, particularly $PgD_2$ and EPA show a remarkable linear correlation with lung function ($r^2>0.7$). The present invention also relates to the measurement of lipid metabolite levels in more easily obtainable biological fluids such as sputum, exhaled air condensate, urine and plasma.

Although the number of samples was relatively small, this analysis demonstrates a good inverse correlation between the levels of $PgD_2$ and EPA measured in BAL fluid by mass spectrometry and several lung function parameters including $FEV_1$, % $FEV_1$ and PEF for $PgD_2$ and $FEV_1$ and % $FEV_1$ in the case of EPA. Furthermore, the correlation between the $FEV_1$ and % $FEV_1$ values and the level of $PgD_2$ was independent of total lung capacity, suggesting that this correlation is strongly associated with the lung function parameter being measured.

Many different classes of mediators of inflammation have been shown to play a role in COPD, including a number of lipids, chemokines and cytokines [Barnes et al., 2004]. In some cases, similar mechanisms of inflammation are shared between COPD and asthma whereas in other cases, some mechanisms are unique to one or the other disease [Jeffrey et al., 2000; Welte et al., 2006]. These mediators play a role in both the recruitment and activation of inflammatory cells [Barnes et al., 2004]. COPD is characterized by the presence in the lungs of macrophages, neutrophils and $CD^8+$ T-cells, whereas in asthma the dominant inflammatory cell types present in the lungs include eosinophils, mast cells and $CD^4+$ lymphocytes indicative of a largely allergic phenotype [Jeffrey et al., 2000].

Prostanoids have been strongly implicated in the pathophysiology of both asthma and COPD [Rolin et al., 2006]. In the case of COPD, most attention has focused on $PgE_2$ which is elevated in the exhaled breath of COPD patients [Montuschi et al., 2003]. $PgE_2$ appears to play both protective and harmful roles in the pathophysiology of COPD [Barnes et al., 2004].

On the one hand, it has been demonstrated to be a bronchodialator [Pavard and Tattersfield, 1995] and to enhance the effects of PDE4 inhibitors (Au et al., 1998), while on the other, it also leads to an increase in mucin gene expression (Borchers et al., 1999) and sensitization and activation of airway sensory nerves, thus enhancing coughing (Stone et al, 1992; Lee et al., 2002). In asthma, the major prostanoid inflammatory mediator is $PgD_2$ [Rolin et al., 2006]. $PgD_2$ is normally secreted by mast cells in response to activation by binding to IgE through specific receptors, leading to bronchoconstriction, and perhaps also to the recruitment of eosinophils and $CD^4+T$ cells [Rolin et al., 2006].

Mast cells have mostly been studied in the context of asthma. A role of mast cells in COPD has been never reported. Ekberg-Jansson et al., 2005, describe that asymptomatic smokers already exhibit a significant increase in the number of mast cells compared to non smokers in multiple compartments of mid-level bronchioles including in the epithelium, smooth muscle and lamina propria as assessed by immunohistochemistry of bronchial biopsies.

Furthermore, there is an increase in the number of mast cells found in bronchial epithelium of smokers with COPD compared to asymptomatic smokers as assessed by cytological examination of pneumectomy specimens removed during lung cancer surgery (Grashoff et al., 1997). Finally, COPD patients challenged with hypertonic saline demonstrated bronchoconstriction and lung hyperinflation which correlated with the presence of elevated histamine levels in sputum samples strongly suggesting a role for mast cells (Taub et al, 2001).

Our data suggest for the first time that mast cells are present in the airways of COPD patients which is consistent with the observed presence of elevated PgD2 levels in the BAL fluid. Overall, these results indicate that PgD2 levels in the lungs, and to a lesser extent those of EPA, may correlate with certain lung function parameters (in particular FEV1) revealing a potential link between inflammation and lung function in COPD. Validation of these results on larger cohorts could suggest new modalities for the treatment of COPD focused on inhibiting either the synthesis of PgD2 and/or EPA or the binding of these ligands to their respective receptors.

In a preferred embodiment, the present invention relates to a method of detecting and/or monitoring chronic obstructive pulmonary disease (COPD) in a subject, the method comprising measuring the level of at least one lipid metabolite selected from prostaglandin D2 and eicosapentanoic acid (EPA), in a sample from the subject, wherein said level is indicative of COPD.

Within the context of the present invention, the terms "lipid metabolites" and "lipid mediators" are used interchangeably.

In another preferred embodiment, the present invention relates to a method of assessing the efficacy of a COPD treatment in a subject, the method comprising a step of measuring the level of at least one lipid metabolite selected from prostaglandin D2 and eicosapentanoic acid (EPA), in a sample from the subject, wherein said level is indicative of COPD severity or status.

In one aspect of the invention, the lipid biomarker level is measured at different time point during treatment, to assess variations thereof during treatment.

In another aspect of the invention, the lipid mediator, metabolite or biomarker is prostaglandin D2 (PgD2). In another aspect of the invention, the lipid metabolite or biomarker is eicosapentanoic acid (EPA).

In specific embodiments, the body fluid or sample is bronchoalveolar lavage, plasma, serum or sputum. In another particular embodiment, the body fluid or sample is exhaled air exudate.

In another embodiment, the present invention relates to a method of measuring one or more lipid metabolites as diagnostic marker.

In another aspect of the invention, the method to measure the lipid metabolite or lipid biomarker is based on mass spectrometry.

The present invention also provides a method to measure lipid metabolite(s), which is based on antibodies specific for the lipid metabolite(s). In variants, these antibodies have been raised in mice or in rabbits.

In a further aspect of the present invention, the progress of COPD is measured by lung function tests. In a particular embodiment, the lung function test is forced expiratory volume in 1 second (FEV1). In another particular embodiment, the lung function test is the % FEV1 compared to a reference value.

The following examples are given for purposes of illustration and not by way of limitation.

EXAMPLES

Materials and Methods:
Patient Recruitment, BAL Fluid Collection:
Patient BAL fluid samples were obtained from the Department of Pulmonology, Medical and Health Science Center, University of Debrecen (Hungary). The clinical protocol was prepared in compliance with EU regulations and the necessary approval was obtained from the regional and Institutional Ethics Committees. Patient selection was driven by lung function tests: forced expiratory volume, first second ($FEV_1$)<80% predicted. Bronchofiberoscopy with BAL was performed as described previously (Clinical guidelines and indications for bronchoalveolar lavage (BAL): Report of the European Society of Pneumology Task Group on BAL. *Eur Respir J.* 1990 September; 3(8):937-76). Briefly, after local anesthesia of the upper respiratory tract with topical lidocaine spray (2%), the tip of the bronchoscope was wedged into a subsegment of the right middle lobe, and 6 serial aliquots of sterile saline, 50 ml each, were introduced and immediately aspirated. Afterwards, the volume of the recovered lavage fluid was measured.

Lipid Metabolite Assays:

Entire BAL samples were extracted with ethyl-acetate (EE) at a ratio of 1:1. The EE extract was dried down in a speedvac under vacuum (Eppendorf concentrator 5301, Eppendorf, Germany) at 30° C. The dried down material was reconstituted in 100 µl methanol, centrifuged and the supernatant was again dried down in the speedvac. The resulting material was reconstituted in 60 µl ethanol and 6 µl isotope mix in methanol (the isotope mix consisted of $d_8$-15-HETE and $d_4$-$PgD_2$) and 10 µl of the extract was analyzed immediately by HPLC-MS.

The HPLC-MS analysis was performed using an HPLC-MS system similar to one reported previously [6] consisting of a Waters 2695X HPLC separation module (Waters, Budapest, Hungary) including a gradient pump, a degasser and a heatable column compartment. The column for this lipid analysis was a Supersher endcapped 100 RP-18 packed LiChroCART 125 mm×2 mm column including a LiChroCART guard column filled with the same material as the separation column from Merck KGaA (Darmstadt, Germany) The column was maintainted at 40° C. and connected directly to the MS-MS detector (Micromass Quatro micro QAA0029 from Waters Budapest, Hungary) including an electospray ionization option (ESI from Waters, Hungary). The system was controlled via the MassLynx software (Waters, Hungary)

The HPLC multilinear gradient was generated using solvents A (water:acetonitrile:formic acid/67:33:0.02) and B (methanol) with the following steps: 0.0 min 20% B, 3 min 20% B, 5 min 60% B, 15 min 100% B, 19.5 min 100% B and 20 min 5% B. The flow was adjusted to 0.2 ml/min with a runtime of 25 min. In a typical HPLC run $PGE_2$ could be base-line separated from $PgD_2$.

MRM (multiple reaction monitoring) with ESI (ESI (−) settings) was performed with the HPLC eluate flowing into the ESI source at a temperature of 85° C. The desolvation gas flow rate was 400 L/h with a desolvation temperature of 400° C. and a cone gas flow rate of 20 L/h. The cone voltage setting was 32 V, the extractor voltage 3V, the RF lens voltage 3.8 V and the capillary voltage 2.49 V. The MS-MS analyzer settings were LM1 resolution 14.6, HM1 resolution 14.6, ion energyl −1.7, entrance reaction chamber −1, collision 10 (collision parameters are set and applied for each substance at the following MS-method parameters), exit of the reaction chamber 2, LM2 resolution 13.0, HM2 resolution 13.0, ion energy 5.7 and a multiplier energy of 650 V.

MRM settings for lipid quantification were: $PgD_2$ 350.9→270.8, collision energy 17 V, cone voltage 22V, dwell time 3 sec; 15-HETE 319.0→218.9, collision energy 11V, cone voltage 25V, dwell time 3 sec; EPA 301→203.2, collision energy 12 V, cone voltage 39 V, dwell time 3 sec. This HPLC MS-MS method was also established for 33 additional PUFAs and eicosanoid for serum as well as analysis of cell pellets (Rühl, in preparation). Stock solutions of lipid standards were prepared from commercially available standards of 15-HETE, dX-15-HETE, dX-$PgD_2$ and $PgD_2$ (Cayman chemicals Co., Ann Arbor, USA) and EPA from Larodan Fine chemicals AB (Malmö, Sweden) to give a final concentration of 1000 ng/ml. All stock solutions were stored in the dark at −80° C. Multilinear calibration was carried out using the reference retinoids by measuring different injections of ethanolic standard solutions at four different concentrations (1, 10, 100, 1000 ng/ml) using a 1 µl injection volume. The detection limit was 5 ng/ml for 15-HETE and EPA, and 10 ng/ml for $PgD_2$ with a linear coefficient of regression of greater than 0.99 over the entire concentration range.

Pulmonary Function Tests

Lung function test: Using a pneumotachograph based system (Piston Body Plethysmography), inspiratory vital capacity, $FEV_1$, and static volumes were determined. Measurements were performed repeatedly until values within 5% variation were obtained at least 2 times. The tests were performed within the ETS, GOLD reproducibility criteria. Spirometry was performed in accordance with the European Respiratory Society and the European Coal and Steel Community standards. The tests were performed when the patients were clinically stable and free from infection. Patients had not used inhaled short-acting bronchodilators in the previous 6 hours, long acting agonists in the previous 12 hours, nor sustained release theophyllines in the preceeding 24 hours.

Bronchodilator reversibility testing: First, pre-bronchodilator spirometry was performed. Subjects were then treated with 400 µg of salbutamol by inhalation, and after 15 minutes post-bronchodilator spirometry was performed. In order for the subject to be designated as having irreversable airway obstruction, the post bronchodilator $FEV_1$/FVC should remain <0.7, and the $FEV_1$ may not improve more than 12% or 200 mL in $FEV_1$, over the pre-bronchodilator value. (Global Initiative for Chronic Obstructive Lung Disease, Global strategy for the diagnosis, management and prevention of Chronic Obstructive Lung Disease. www.goldcopd.com)

Results:

As presented in table 1 below, the pulmonary function results shown here clearly segregate the two patient populations, one with, the other without COPD.

TABLE 1

Statistically significant difference between COPD and Control groups: $FEV_1$.

|  | COPD | Control | p < 0.01 |
|---|---|---|---|
| Age | 58.5 ± 4.43 | 57.50 ± 5.00 |  |
| $FEV_1$ | 61.73 ± 5.68 | 95.63 ± 2.79 |  |
| $FEV_1$/FVC | 64.10 ± 3.28 | 82.18 ± 1.49 |  |
| IVC | 3.28 ± 0.16 | 3.86 ± 0.42 |  |

The differences are statistically significant for $FEV_1$, $FEV_1$/FVC, and IVC. In an initial attempt to find correlations between lipid metabolite levels and lung function we plotted the concentrations of several lipid metabolites found in the BAL fluid of the test subjects against numeric values of various pulmonary function tests and determined the $R^2$ values.

The lipids which were used in this determination were those that gave measurable values in most or all of the BAL fluid samples tested and include eicosapentaenoic acid (EPA), lysophosphatidyl choline (LPC), 15 hydroxyeicosatetranoic acid (15-HETE) and prostaglandin D2 ($PgD_2$). The results are shown in FIG. 1.

The lung function parameters which were used in the analysis include the forced expiratory volume in 1 second ($FEV_1$), the $FEV_1$ compared to the theoretical value (% $FEV_1$), the peak expiratory flow (PEF) and the total lung capacity (TLC).

We noted that although all patients received a similar amount of lavage fluid via a flexible bronchosope, the recovered fraction of the fluid was variable and we found no apparent correlation between the estimated metabolite concentration and the results of the lung function test with the exception of total lung capacity.

The $R^2$ values are given for each of the metabolites in table 2A and an example of the plots is given for $PgD_2$ in FIG. 2. There was also a strong correlation between the total amount of certain recovered analytes and the amount of BAL fluid recovered, in particular EPA ($R^2=-0.77$) and 15-HETE ($R^2=-0.75$), and to a lesser extent $PgD_2$ ($R^2=-0.57$).

TABLE 2

R2 values and lipid metabolites: lipid concentration (A), total recovered lipid amount (B), normalized (to TLC) total recovered lipid amount (C).

|   | lipid/lung function | % FEV | FEV | PEF | TLC |
|---|---|---|---|---|---|
| A | PgD2 | −0.509 | −0.401 | −0.406 | 0.778 |
|   | EPA | −0.228 | −0.228 | −0.311 | 0.779 |
|   | LPC | −0.385 | −0.386 | −0.067 | 0.644 |
|   | 15-HETE | −0.544 | −0.479 | −0.19 | 0.644 |
| B | PgD2 | −0.665 | −0.647 | −0.702 | 0.372 |
|   | EPA | −0.705 | −0.628 | −0.365 | 0.698 |
|   | LPC | −0.461 | −0.403 | −0.213 | 0.716 |
|   | 15-HETE | −0.513 | −0.498 | −0.202 | 0.517 |
| C | PgD2 | −0.672 | −0.771 | −0.584 | 0 |
|   | EPA | −0.575 | −0.511 | −0.541 | 0 |
|   | LPC | −0.487 | −0.443 | −0.255 | 0 |
|   | 15-HETE | −0.513 | −0.504 | −0.209 | 0 |

These observations have prompted us to develop a hypothetic model of BAL fluid compartmentalization. We assume that the delivered lavage fluid partitions to two compartments: in compartment-1, which can be called "recoverable", the fluid reaches the target tissue environment and a sufficient degree of equilibration of soluble metabolites and particles takes place at this site. The recoverable compartment is likely represented by the large and mid-size bronchi. The fraction of metabolites present in the recoverable compartment and which equilibrate with the lavage fluid is assumed to be fairly constant. Consequently, it is the total recovered lipid metabolite amount and not the concentration of the metabolite, which may show correlation with functional parameters. The second compartment, named "non-recoverable" may not interfere with the metabolite recovery from the recoverable compartment. The non-recoverable compartment is likely represented by the bronchoalveolar space. It is likely that the majority of the liquid from this compartment is reabsorbed. Variability of the compartment size could be due to variation in BAL technique, individual differences and re-absorption speed. Likely this latter factor has the highest impact.

To consider our model, the lung function values were plotted against the total recovered BAL lipid levels for each of the four lipids. All values were used except for the value of EPA for control subject 8026 which may be an outlier (please see FIG. 1). The $R^2$ values for this analysis are presented in table 2B and an example of the plots for $PgD_2$ is shown in FIG. 3.

For $PgD_2$ there is a striking inverse correlation between the total recovered in the BAL fluid and $FEV_1$, % $FEV_1$ and PEF which in all cases gave a value above 0.6. On the other hand, there was no correlation between $PgD_2$ levels and total lung capacity. Of the other analytes, only EPA showed an inverse correlation between the amount in BAL fluid and $FEV_1$ and % $FEV_1$.

Given the relatively strong correlation between total lung capacity and both the concentration of lipids recovered in BAL fluid as well as total lipid recovery the total recovered lipid values were normalized as a function of lung capacity and reanalyzed. The $R^2$ values from the reanalyzed data are shown in table 2C. The values obtained following this analysis demonstrate that the correlation between $PgD_2$ levels and the $FEV_1$ and % $FEV_1$ values are independent of total lung capacity (FIG. 4) whereas the correlations between $PgD_2$ and PEF as well as EPA and all of the lung function parameters were slightly dependent upon this parameter. The correlations for LPC and 15-HETE were not substantially affected.

References

Rabe, K. F., Hurd, S., Anzueto, A., Barnes P. J., et al., *Am J. Respir. Crit. Care Med.* 2007, 176, 535-555.

Rennard, S. I., Barnes, P. J., in: Barnes, P. J., Drazen, J. M., Rennard, S., Thomson, N. C. (Eds.), *Asthma and COPD: Basic mechanisms and clinical management*, Academic Press, New York, 2002, pp 362-379.

Hogg, J. C., Utokaparch, S., Yamada Y, Elliott, W. M., et al., *N. Engl. J. Med.*, 2004, 350, 2645-2353.

Barnes, P. J., *Pharmacol. Rev.*, 2004, 56, 515-548.

Csanky, E., Olivova, P., Rajnavolgy, E., Hempel, W., et al., *Electrophoresis*, 2007, 28, 4401-4406.

Rühl, R., *Rapid. Commun. Mass Spectrom.*, 2006, 20, 2497-2504.

Jeffrey, P. K., *Chest*, 2000, 117, 251S-260S.

Welte, T., Groneberg, D. A., *Exp. Toxicol. Pathol.*, 2006, 57S2, 35-40.

Rolin, S., Maseree, B., Dogneé, J-M., *Eur. J. Pharmacol.*, 2006, 533, 89-100.

Montuschi, P., Kharitonov, S. A., Ciabattoni, G., Barnes, P. J., *Thorax*, 2003, 58, 585-588.

Pavard, I D and Tattersfield A E (1995) Bronchoprotective role for endogenous prostaglandin $E_2$. *Lancet* 344:436-438.

Au B T, Teixeira M M, Collins P D, and Williams T J (1998) Effect of PD4 inhibitors on zymosin induced IL-8 release from human neutrophils: synergism with prostanoids and salbutamol. *Br. J. Pharmacol.* 123:1260-1266.

Borchers M T, Cary M P, and Leikauf G D (1999). Regulation of human airway mucins by acrolein and inflammatory mediators. *Am. J. Physiol.* 276:L549-L555.

Ekberg-Jansson A, Amin K, Bake B, Rosengren A, Tylén U, Venge P, and Löfdahl CG (2005) Bronchial mucosal mast cells in asymptomatic smokers relation to structure, lung function and emphysema. *Resp. Med.* 99:75-83.

Grashoff W F H, Sont J K, Sterk P J, Hiemstra P S, de Boer W I, Stolk J, and van Krieken J M (1997) Chronic Obstructive Pulmonary Disease: Role of bronchiolar mast cells and macrophages. *Am. J. Pathol.* 151:1785-1790.

Hurd S. (2000) The impact of COPD on lung health worldwide: epidemiology and incidence. *Chest* 117:1S-4S.

Lee L Y, Kong K., Lin Y S, and Gu Q (2002) Hypersensitivity of bronchopulmonary C-fibres induced by airway mucosal inflammation: cellular mechanisms. *Pulm. Pharmacol. Ther.* 15:199-204.

Romagnoli M, Richeldi L, and Fabbri, L M (2002) Clinical Assessment of astma and COPD: Diagnosis. In Asthma and COPD: Basic mechanisms and clinical management, eds. Barnes P J, Drazen J M, Rennard S, and Thomson N C, Academic Press. Pp 447-455.

Stone R, Barnes P J, and Fuller R W (1992) Contrasting effects of prostaglandin $E_2$ and $F_2$ on sensitivity of the human cough reflex. *J. Appl. Physiol.* 73:649-653.

Taub C., Holz, O, Mücke M, Jörres R A, and Magnussen H (2001) Airway response to inhaled hypertonic saline in patients with moderate to severe chronic obstructive pulmonary disease. *Am. J. Respir. Crit. Care Med.* 164: 1810-1815.

The invention claimed is:

1. A method of detecting and/or monitoring chronic obstructive pulmonary disease (COPD) in a subject, the method comprising obtaining a bodily sample or fluid from a subject and measuring the level of at least one lipid metabolite selected from prostaglandin D2 and eicosapentanoic acid (EPA), wherein said level is indicative of COPD.

2. The method of claim 1, wherein the lipid biomarker level is measured at different time point during treatment, to assess variations thereof during treatment.

3. The method of claim 1, wherein the lipid metabolite or biomarker is prostaglandin D2 (PgD2).

4. The method of claim 1, wherein the lipid metabolite or biomarker is eicosapentanoic acid (EPA).

5. The method of claim 1, wherein the body fluid or sample is bronchoalveolar lavage.

6. The method of claim 1, wherein the body fluid or sample is plasma or serum.

7. The method of claim 1, wherein the body fluid or sample is sputum.

8. The method of claim 1, wherein the body fluid or sample is exhaled air exudate.

9. The method of claim 1, wherein the lipid metabolite is measured by mass spectrometry.

10. The method of claim 1, wherein the lipid metabolite is measured by the binding of antibodies specific for the lipid metabolite.

11. The method of claim 1, further comprising measuring the progress of COPD by lung function tests.

12. The method of claim 11, wherein the lung function test is forced expiratory volume in 1 second (FEV1).

13. The method of claim 11, wherein the lung function test is the % FEV1 compared to a reference value.

14. A method of assessing the efficacy of a COPD treatment in a subject, the method comprising a step of measuring the level of at least one lipid metabolite selected from prostaglandin D2 and eicosapentanoic acid (EPA), in a sample from the subject, wherein said level is indicative of COPD severity or status.

15. The method of claim 14, wherein the lipid biomarker level is measured at different time point during treatment to assess the efficacy of said treatment.

16. The method of claim 14, wherein the lipid metabolite or biomarker is prostaglandin D2 (PgD2).

17. The method of claim 14, wherein the lipid metabolite or biomarker is eicosapentanoic acid (EPA).

18. The method of claim 14, wherein the lipid metabolite is measured by mass spectrometry.

19. The method of claim 14, wherein the lipid metabolite is measured by the binding of antibodies specific for the lipid metabolite.

* * * * *

UNITED STATES PATENT AND TRADEMARK OFFICE
CERTIFICATE OF CORRECTION

PATENT NO. : 8,501,422 B2
APPLICATION NO. : 13/120189
DATED : August 6, 2013
INVENTOR(S) : Csanky Eszter et al.

Page 1 of 1

It is certified that error appears in the above-identified patent and that said Letters Patent is hereby corrected as shown below:

In the Specification

Column 1,
Line 61, "www.goldcopd.corn)." should read --www.goldcopd.com).--.

Column 6,
Line 40, "www.goldcopd. corn)" should read --www.goldcopd.com).--.

Column 8,
Line 35, "Dogneé," should read --Dogné,--.

Signed and Sealed this
Twenty-sixth Day of November, 2013

Margaret A. Focarino
*Commissioner for Patents of the United States Patent and Trademark Office*